(12) United States Patent
Plouzek (10) Patent No.: US 10,578,590 B2
(45) Date of Patent: Mar. 3, 2020

(54) ULTRASONIC WEAR LIFE SENSING OF GROUND ENGAGING TOOLS

(71) Applicant: Caterpillar Inc., Peoria, IL (US)

(72) Inventor: John Michael Plouzek, Peoria, IL (US)

(73) Assignee: Caterpillar Inc., Peoria, IL (US)

( * ) Notice: Subject to any disclaimer, the term of this patent is extended or adjusted under 35 U.S.C. 154(b) by 0 days.

(21) Appl. No.: 16/456,415

(22) Filed: Jun. 28, 2019

(65) Prior Publication Data

US 2019/0317052 A1 Oct. 17, 2019

Related U.S. Application Data

(63) Continuation of application No. 15/423,247, filed on Feb. 2, 2017, now Pat. No. 10,371,669.

(51) Int. Cl.
| | |
|---|---|
| *G01N 29/44* | (2006.01) |
| *E02F 9/28* | (2006.01) |
| *G01N 29/24* | (2006.01) |
| *G01N 29/07* | (2006.01) |
| *G01N 29/22* | (2006.01) |
| *G01N 17/04* | (2006.01) |
| *G01N 17/00* | (2006.01) |

(52) U.S. Cl.
CPC ....... *G01N 29/4454* (2013.01); *E02F 9/2808* (2013.01); *E02F 9/2883* (2013.01); *G01N 17/006* (2013.01); *G01N 17/04* (2013.01); *G01N 29/07* (2013.01); *G01N 29/223* (2013.01); *G01N 29/2475* (2013.01); *G01N 29/4445* (2013.01); *G01N 2291/011* (2013.01); *G01N 2291/0258* (2013.01)

(58) Field of Classification Search
CPC .. E02F 9/2808; E02F 9/2883; G01N 29/4454; G01N 29/07; G01N 29/2475; G01N 29/223; G01N 29/4445; G01N 17/04; G01N 17/006
See application file for complete search history.

(56) References Cited

U.S. PATENT DOCUMENTS

2014/0311762 A1* 10/2014 Behmlander ......... E02F 3/8152
172/430

* cited by examiner

*Primary Examiner* — Paul M. West
(74) *Attorney, Agent, or Firm* — Hibshman Claim Construction PLLC (57) ABSTRACT

A ground engaging member that engages a work material to dig into the work material includes a member body extending from a leading end to a trailing end, the member body having an internal surface defining a cavity therein, the cavity having a concavity that faces away from the leading end along a longitudinal direction, the longitudinal direction extending from the leading end to the trailing end; and a first wear sensing body embedded in the member body between the cavity and the leading end along the longitudinal direction. The member body is fabricated from a ground engaging tool (GET) body material having a GET body material density. The first wear sensing body is fabricated from a wear sensing body material having a wear sensing body material density that is not equal to the GET body material density.

20 Claims, 7 Drawing Sheets

ULTRASONIC WEAR LIFE SENSING OF GROUND ENGAGING TOOLS

CROSS-REFERENCE TO RELATED APPLICATIONS

This application is a Continuation of U.S. application Ser. No. 15/423,247, filed on Feb. 2, 2017, the disclosure of which being hereby incorporated by reference in its entirety.

TECHNICAL FIELD

The present disclosure relates generally to earth working machines with ground engaging implements and, in particular, to wear detection in wear surfaces and ground engaging tools (GETs) of such ground engaging implements to determine when the wear surfaces and GETs reach the ends of their useful wear lives.

BACKGROUND

Earth moving machines known in the art are used for digging into the earth or rock and moving loosened work material from one place to another at a worksite. The machines and equipment include articulating mechanical arms or other types of linkages for manipulating one or more implements of the machine. The linkages are capable of raising, lowering and rotating the implements to engage the ground or other work material in a desired manner. In the earth moving applications, the implements of the machines or other equipment may be buckets provided with a beveled lip or blade on a base edge for moving or excavating dirt or other types of work material. In other applications, implements can include rippers, blades, thumbs and the like that dig into the work material.

To facilitate the earth moving process, and to prolong the useful life of buckets and similar implements, a plurality of tooth assemblies may be spaced along the material engaging edge of the implement and attached to the surface of the implement. The tooth assemblies project forward from the material engaging edge as a first point of contact and penetration with work material, and to reduce the amount of wear of the material engaging edge. With this arrangement, the tooth assemblies are subjected to the wear and breakage caused by repetitive engagement with the work material. Eventually, the tooth assemblies must be replaced, but the implement remains usable through multiple cycles of replacement tooth assemblies. Other types of GETs may be attached to buckets or other implements at points where the most wear is expected to occur, such as edge protectors, corner guards, cutting edges and the like.

In many implementations, installation and replacement of the tooth assemblies may be facilitated by providing the tooth assemblies as a two-part system. The system may include an adapter that is attached to the material engaging edge of the implement, a ground-engaging tip configured to be attached to the adapter, and a retention mechanism securing the tip to the adapter during use. The adapter may be welded, bolted or otherwise secured to the base edge, and then the tip may be attached to the adapter and held in place by the retention mechanism. The tip endures the majority of the impact and abrasion caused by engagement with the work material, and wears down more quickly and breaks more frequently than the adapter. The point at a tip is worn down to the point that its useful life is exhausted and the tip should be replaced may be known in the abstract, but it may be difficult to determine in the field that the tip has reached that point.

One example of a strategy for monitoring the wear on a ground engaging tip is illustrated and described in U.S. Pat. Appl. Publ. No. 2015/0149049 A1 to Bewley et al. The Bewley et al. publication discloses a process and tool for monitoring the status, health, and performance of wear parts used on earth working equipment. In one embodiment, a monitoring system has one or more electronic sensors to determine a current length of a wear member on an edge of a bucket. The monitoring system is installed on a bridge or top of the bucket, and electronic sensors have a clear line of sight to the wear members during use. Features may be incorporated onto the wear member to aid in determining the degree the wear member has been worn. The wear member may contain multiple features along the length of the expected wear profile so that as the wear member wears, the monitoring system is able to detect the number of features remaining on the wear member.

SUMMARY OF THE DISCLOSURE

According to an aspect of the present disclosure, a ground engaging member includes a member body extending from a leading end to a trailing end, the member body having an internal surface defining a cavity therein, the cavity having a concavity that faces away from the leading end along a longitudinal direction, the longitudinal direction extending from the leading end to the trailing end, the member body being fabricated from a ground engaging tool (GET) body material having a GET body material density; and a first wear sensing body embedded in the member body between the cavity and the leading end along the longitudinal direction, the first wear sensing body being fabricated from a wear sensing body material having a wear sensing body material density that is not equal to the GET body material density.

According to another aspect of the present disclosure, a ground engaging assembly includes a plurality of member bodies, each member body of the plurality of member bodies extending from a leading end to a trailing end, each member body having an internal surface defining a cavity therein, the cavity having a concavity that faces away from the leading end along a longitudinal direction, the longitudinal direction extending from the leading end to the trailing end, each member body being fabricated from a ground engaging tool (GET) body material having a GET body material density; and a first wear sensing body embedded in each member body between the cavity and the leading end along the longitudinal direction, the first wear sensing body being fabricated from a wear sensing body material having a wear sensing body material density that is not equal to the GET body material density.

According to another aspect of the present disclosure, an implement of a work machine includes a plurality of member bodies, each member body of the plurality of member bodies extending from a leading end to a trailing end, each member body having an internal surface defining a cavity therein, the cavity having a concavity that faces away from the leading end along a longitudinal direction, the longitudinal direction extending from the leading end to the trailing end, each member body being fabricated from a ground engaging tool (GET) body material having a GET body material density; and a first wear sensing body embedded in each member body between the cavity and the leading end along the longitudinal direction, the first wear sensing body being fabricated from a wear sensing body material having a wear sensing body material density that is not equal to the GET body material density.

DETAILED DESCRIPTION

Figure 1:
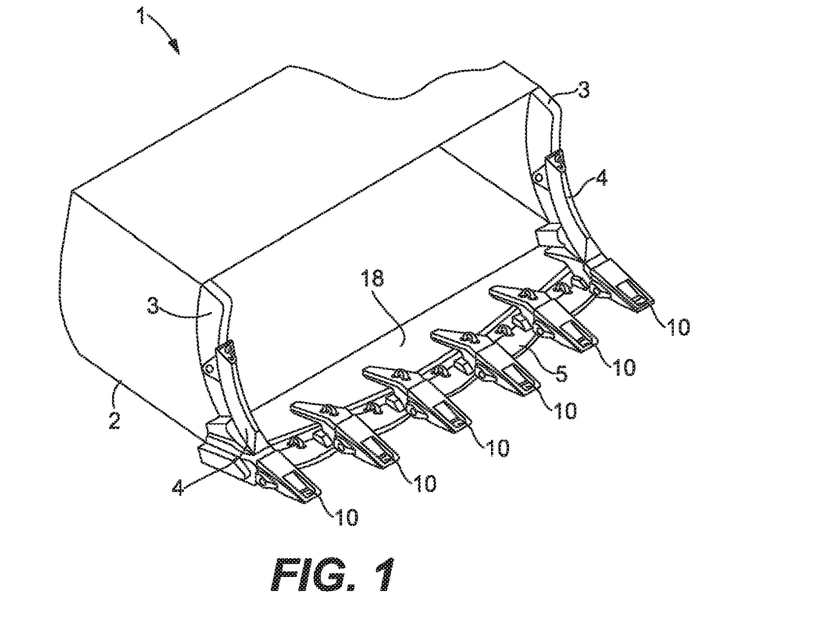
FIG. 1 is an isometric view of a loader bucket having GETs attached thereto.
Figure 2:
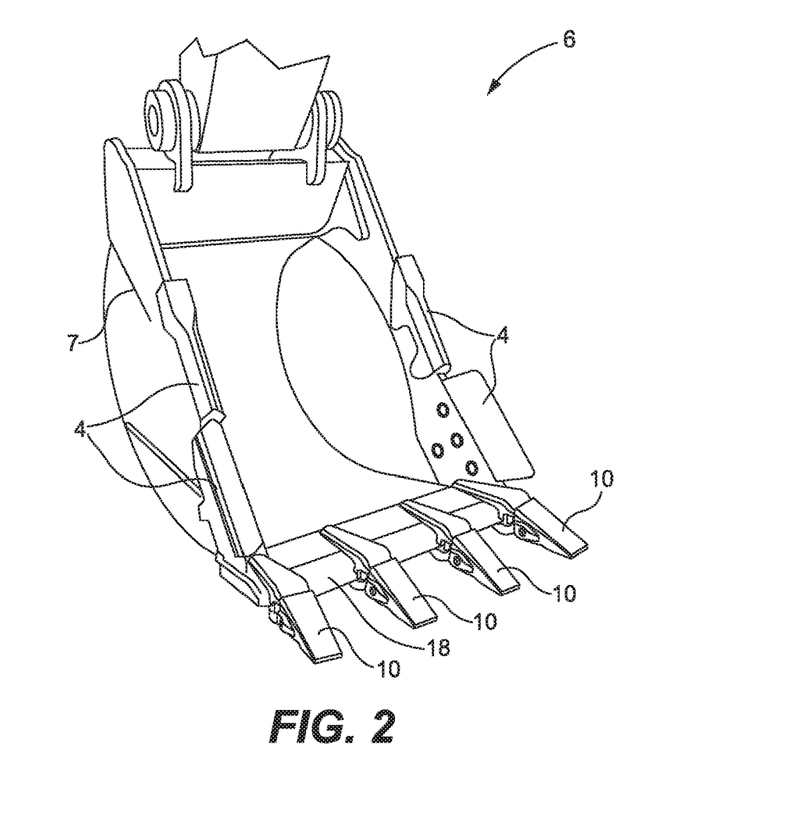
FIG. 2 is an isometric view of an excavator bucket having GETs attached thereto.

Referring now to FIG. 1, there is shown an implement for a bottom-wearing application, such as a loader machine, in the form of a loader bucket assembly 1. The loader bucket assembly 1 includes a loader bucket 2 which is partially shown in FIG. 1. The loader bucket 2 is used on the loader machine to excavate work material in a known manner. The bucket assembly 1 may include several GETs including a pair of oppositely-disposed support arms 3 on which corresponding corner guards 4 may be mounted. The bucket assembly 1 may further included a number of edge protector assemblies 5 interposed between tooth assemblies 10, with the edge protector assemblies 5 and the tooth assemblies 10 being secured along a base edge 18 of the loader bucket 2. FIG. 2 illustrates an implement for a top-wearing application, such as an excavator, in the form of an excavator bucket assembly 6. The excavator bucket assembly 6 includes an excavator bucket 7 having corner guards 4 connected on either side, and a plurality of tooth assemblies 10 attached across the base edge 18 of the excavator bucket 7. Various embodiments of tooth assemblies 10 may be described herein that may be implemented in bottom-wearing and top-wearing applications. However, those skilled in the art will understand that wear life sensing systems an accordance with the present disclosure may be implemented in many different configurations of tooth assemblies 10 and in implements used in diverse bottom-wearing and top-wearing implementations. Moreover, the wear life sensing systems may be implemented in a similar manner in other GETs for implements that experience wear such as the corner guards 4, the edge protector assemblies 5, and the base edge 18, as well as GETs on other types of implements. The illustration and description of the wear life sensing system in the tooth assemblies 10 is exemplary, and those skilled in the art will understand how to implement the wear life sensing system in other GETs based on the disclosure provided herein.

Figure 3:
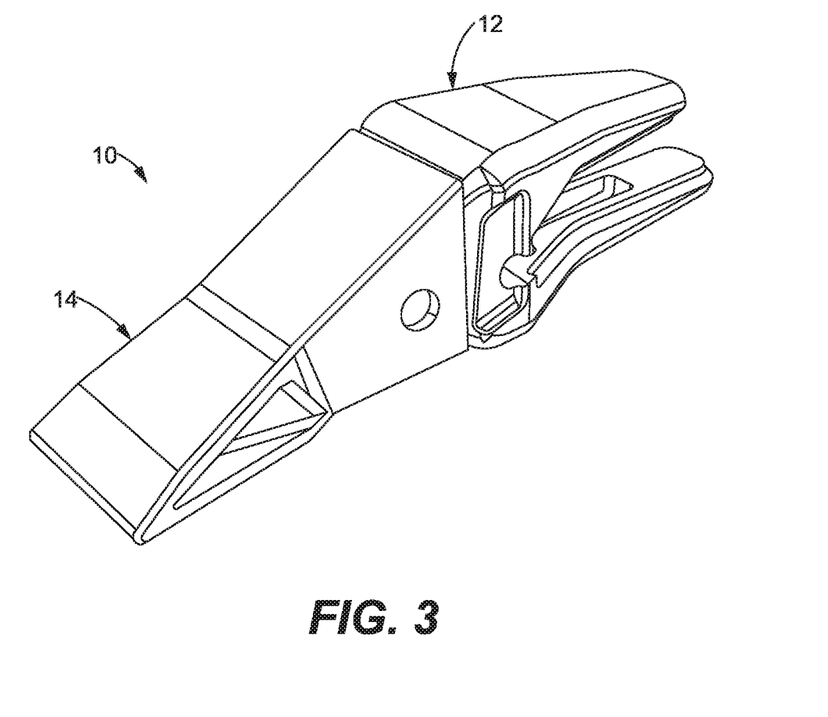
FIG. 3 is an isometric view of an exemplary GET in the form of a tooth assembly that may incorporate a wear life sensing system in accordance with the present disclosure.
Figure 4:
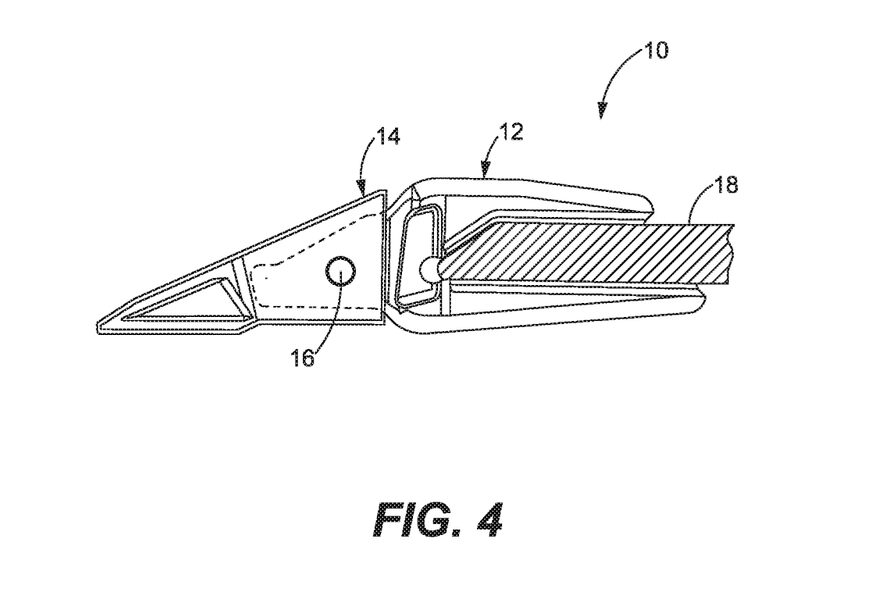
FIG. 4 is a side view of the tooth assembly of FIG. 3.

FIGS. 3 and 4 illustrate an embodiment of an exemplary tooth assembly 10 that may be useful with earth moving implements, and in which a wear life sensing system in accordance with the present disclosure may be implemented. The tooth assembly 10 includes an adapter 12 configured for attachment to the base edges 18 of the implements 2, 7 (FIGS. 1 and 2, respectively), and a ground engaging tip 14 configured for attachment to the adapter 12. The tooth assembly 10 further includes a retention mechanism (not shown) securing the ground engaging tip 14 to the adapter 12. The retention mechanism may utilize aspects of the adapter 12 and the ground engaging tip 14, such as retention apertures 16 through the sides of the ground engaging tip 14, but those skilled in the art will understand that many alternative retention mechanisms may be implemented in the tooth assemblies 10, and the tooth assemblies 10 are not limited to any particular retention mechanism(s). As shown in FIG. 4, once attached to the adapter 12, the ground engaging tip 14 may extended outwardly from the base edge 18 of the implement 2, 7 for initial engagement with the work material (not shown).

Figure 5:
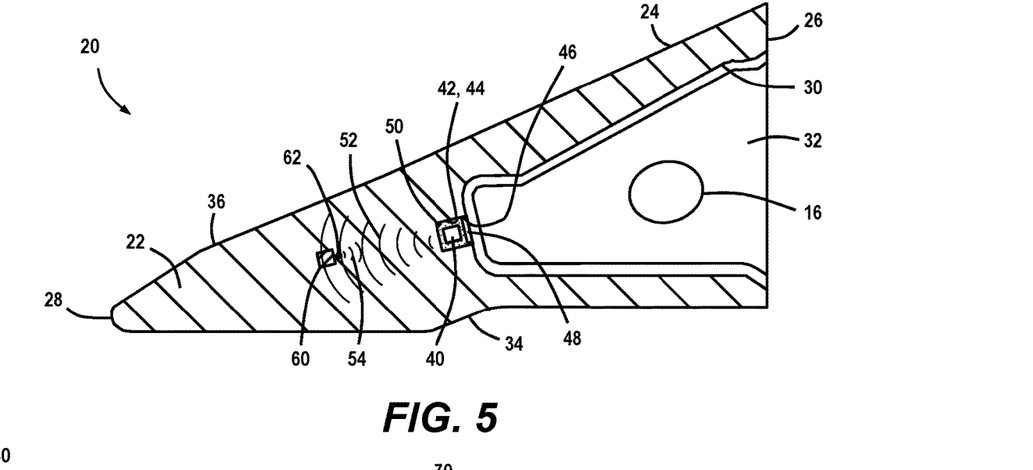
FIG. 5 is a cross-sectional view of a ground engaging tip including a wear sensor assembly and wear sensing body in accordance with the present disclosure.

FIG. 5 illustrates a cross-sectional view of an embodiment of a ground engaging tip 20 in accordance with the present disclosure. The ground engaging tip 20 as shown has a tip body 22 that is generally similar to previously known ground engaging tips for the tooth assemblies 10. The tip body 22 is fabricated from an appropriate GET body material having a hardness to provide the ground engaging tip 20 with a sufficient wear life for the material moving tasks that will be performed and the characteristics of the work material that will be moved. Appropriate materials can include steels of varying harnesses. In applications where sand, gravel or other abrasive materials severely diminish wear life, and additional material such as hard tungsten carbide particles may be bonded to critical wear areas.

The tip body 22 has an exterior surface 24 extending from an adapter connection end 26 and converging to a ground engaging end 28. The adapter connection and 26 includes an adapter cavity surface 30 extending inwardly into the tip body 22 and defining an adapter cavity 32 for receiving an adapter nose (not shown) of the adapter 12 of the ground engaging tooth assembly 10. The ground engaging tip 20 may be secured to the adapter 12 after the adapter nose is inserted into the adapter cavity 32 by attachment hardware inserted through the retention apertures 16 and engaging the adapter nose.

The exterior surface 24 is generally tapered from the adapter connection and 26 to the ground engaging and 28. The exterior surface 24 is contoured to penetrate the work material into which the base edges 18 of the implements will dig, and to match the operations performed by the implements, such as buckets 2, 7. For example, the ground engaging tip 20 may be customized for the loader bucket 2 and will scrape a bottom surface 34 along the ground. Therefore, the tip body 22 may be provided with more material at the bottom surface 34 where more wear is expected, and with relatively less material at a top surface 36 where less wear is expected. In a tip body 22 for the excavator bucket 7 or other top-wearing implementations, more material may be provided at the top surface 36 and relatively less material at the bottom surface 34. In other applications, the exterior surface 24 and the adapter cavity 32 may be approximately symmetrical about a longitudinal axis of the tip body 22 so that the tip body 22 is reversible on the adapter 12 so that one surface 34, 36 can wear during a first period of use, and then the tip body 22 can be flipped over and the opposite surface 34, 36 can wear until the tip body 22 must be replaced.

The ground engaging tip 20 in accordance with the present disclosure is configured so that the wear life, and importantly the point at which the ground engaging tip 20 has reached the end of its useful wear life and should be replaced, can be detected in a timely manner to allow the ground engaging tips 20 to be replaced with minimal interruption to the availability of the implements 2, 7 and the machines on which they are used. Because the actual use of the work machines varies and the characteristics of the work material will vary, the ground engaging tip 20 will wear at different rates, and the material of the tip body 22 will not wear away in a predictable manner. This makes visual inspection difficult, though the point at which the tip body 22 is worn to the end of its useful wear life may be known from the process of designing the ground engaging tip 20. In the ground engaging tip 20 having the wear life sensing system in accordance with the present disclosure, the acoustic properties of the tip body 22 and the material from which it is fabricated may be used to determine when replacement of the ground engaging tip 20 is necessary. Sound can propagate through the material of the tip body 22 and will be reflected when the sound waves experience a change in density, such as when the sound waves reach the exterior surface 24 of the tip body 22. Unfortunately, due to the contours of the exterior surface 24, the sound waves may reflect that an angle and not directly back to the source of the sound waves. Even if the soundwave source is initially oriented normal to a portion of the exterior surface 24, as the tip body 22 wears over time, the contour of the exterior surface 24 will change and will not remain normal with respect to the direction of propagation of the sound waves. Moreover, due to the mixed uses of the implements 2, 7, the tooth assemblies 10 and other GETs on the various work machines and in the various work environments, there is no set wear pattern for the various designs of the exterior surface 24. Consequently, the exterior surface 24 does not serve as a reliable reference for using sound waves for determining a length of the tip body 22 and a corresponding amount of wear that has occurred over time.

The ground engaging tip 20 having the wear life sensing system in accordance with the present disclosure facilitates the use of sound waves within the tip body 22 to determine when the tip body 22 is worn to the end of its useful wear life and is ready for replacement. The tip body 22 is provided with a reference structure within the tip body 22 that will provide a consistent reflection of sound waves over time as the tip body 22 wears. The presence of the reference structure is detectable based on the reflected sound waves until the tip body 22 and the reference structure are worn away and the character of the reflected sound waves changes.

Still referring to FIG. 5, the ground engaging tip 20 may be provided with a wear sensor assembly 40 of the wear life sensing system that is capable of outputting distance sensor signals and receiving and detecting reflected distance sensor signals to determine a distance to an object off of which the distance sensor signals rebound. To accommodate the embedding of the wear sensor assembly 40 within the tip body 22, a wear sensor cavity surface 42 may define a wear sensor cavity 44 that receives the wear sensor assembly 40 therein. As illustrated, the wear sensor cavity 44 is a further recess within the adapter cavity 32. The wear sensor assembly 40 may be inserted through a wear sensor cavity opening 46, and a wear sensor cavity cap 48 may be installed to retain the wear sensor assembly 40 within the wear sensor cavity 44.

While shown in FIG. 5 is extending inward from the adapter cavity 32, the wear sensor cavity surface 42 and the wear sensor cavity 44 may be formed at any appropriate location within the tip body 22. For example, the wear sensor cavity surface 42 may extend inwardly from the bottom surface 34 or the top surface 36 in a location where a relatively light amount of work material engagement and material wear is expected to occur. Alternatively the wear sensor cavity 44 may be located in any other appropriate location within the tip body 22 where the wear sensor assembly 40 can propagate sound waves through the tip body 22 for at least the duration of the wear life of the ground engaging tip 20.

The wear sensor assembly 40 may fit snugly within the wear sensor cavity 44 during use of the ground engaging tip 20. Alternatively, if necessary, the wear sensor assembly 40 may be suspended within the wear sensor cavity 44 in a conductive gel 50. The conductive gel 50 may be a conductive gelatinous substance that is a conductive medium for propagating output distance sensor signals 52 and reflected distance sensor signals 54 through the wear sensor cavity 44. One example of such a conductive gel 50 is the coupling gel used as a conductive medium for the sound waves generated by an ultrasonic transducer. The conductive gel 50 may have a sufficient density and viscosity to suspend the wear sensor assembly 40 in place within the wear sensor cavity 44 while the work machine operates on the work material. In alternative embodiments, other structures may be used to secure the wear sensor assembly 40 in place within the wear sensor cavity 44 and allow or facilitate propagation of the sound waves into the tip body 22.

The ground engaging tip 20 further includes a wear sensing body 60 embedded within the tip body 22. The wear sensing body 60 may be located within the tip body 22 proximate a maximum GET wear point 62. The maximum GET wear point 62 may be identified by the tip designer as the end of the designed wear life of the ground engaging tip 20 after which the ground engaging tip 20 should be replaced. The wear sensing body 60 may be embedded into the tip body 22 during the casting or other fabrication process. For example, the wear sensing body 60 may be formed on a head of a nail (not shown) or other positioning structure within the mold for the tip body 22 so that the GET body material will engulf the wear sensing body 60 when the GET body material is poured into the mold. Alternatively, the wear sensing body 60 may be embedded into the tip body 22 after the tip body 22 is formed, such as by inserting the wear sensing body 60 through a pre-molded or post-molding drilled channel (not shown) into the tip body 22, and with the channel then being backfilled with the GET body material.

To acoustically distinguish the wear sensing body 60 from the tip body 22, the wear sensing body 60 is fabricated from a wear sensing body material having a wear sensing body material density and speed of sound there through that are different from the density and speed of sound through the GET body material. As discussed above, the tip body 22 may be fabricated from hardened steels, which can have densities ranging from 7.75-8.05 g/cm$^3$ (0.28-0.29 ounce/in$^3$), and sounds traveling through the tip body 22 at approximately 6,100 m/s (approximately 20,013 ft/s). In contrast, the wear sensing body 60 may be a piece of carbon or graphite having wear sensing body material densities of approximately 2.25 g/cm$^3$ (approximately 0.08 ounce/in$^3$), and having sound travel through the wear sensing body at approximately 1,470 m/s (approximately 4,823 ft/s). The change in density and speed of sound between the GET body material and the wear sensing body material will cause the echoed or reflected distance sensor signals 54 when the output distance sensor signals 52 encounter the wear sensing body 60. The receipt and the detection of the reflected distance sensor signals 54 at the wear sensor assembly 40 will indicate that the wear sensing body 60 is still present in the tip body 22 and the tip body 22 is not worn to the maximum GET wear point 62. When the tip body 22 is worn down to the maximum GET wear point 62, the wear sensing body 60 will be worn away from the tip body 22 and the characteristics of the reflected distance sensor signals 54 reflected off the worn down exterior surface 24 will allow the wear sensor assembly 40 to determine that the tip body 22 is at the end of its useful wear life and should be replaced as discussed further hereinafter. Those skilled in the art will understand that the wear sensing body 60 may be fabricated from any other appropriate material that will cause a reflection of the output distance sensor signals 52. In further embodiments, an air pocket could be formed within the tip body 22 proximate the maximum wear point 62, with the change in density from the GET body material and the air causing a similar reflection of the output distance sensor signals 52.

Figure 6:
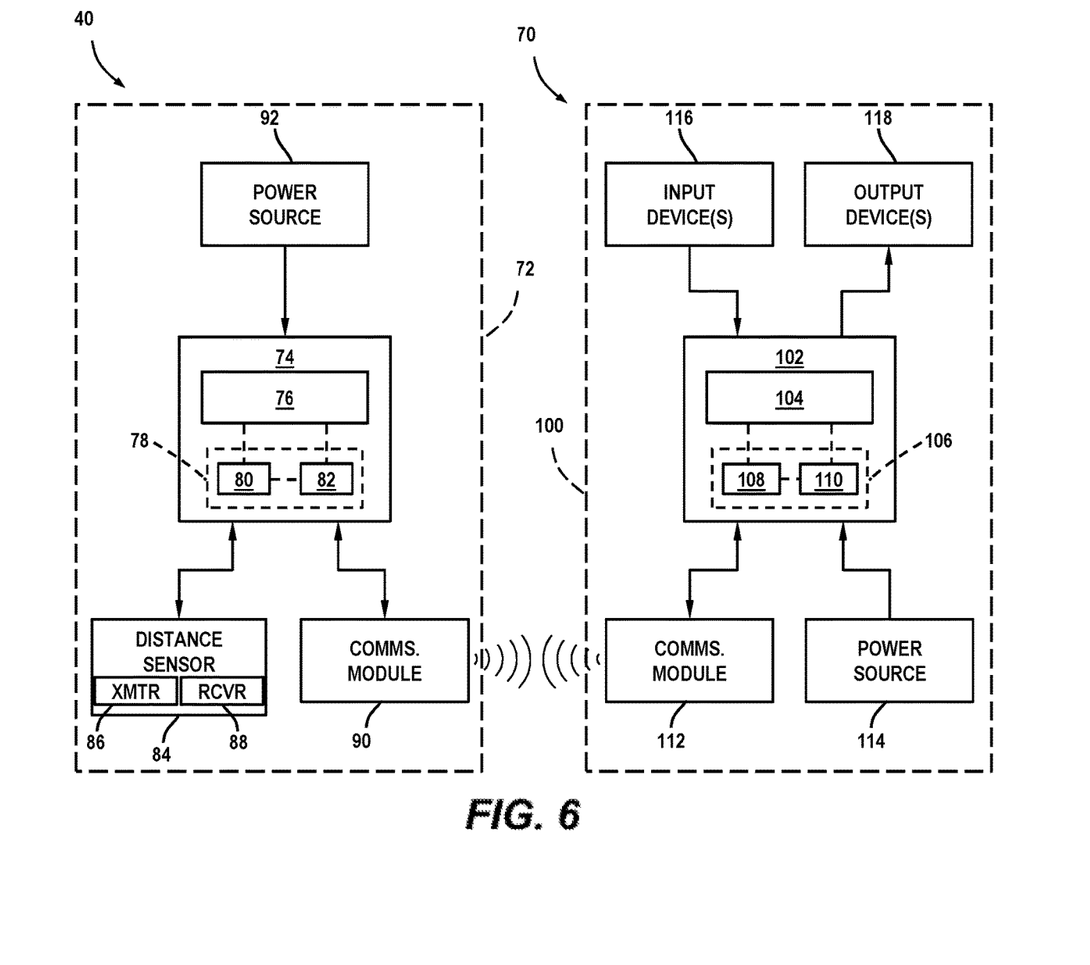
FIG. 6 is a schematic illustration of electrical and control components of the wear sensor assembly of the wear life sensing system of FIG. 5 and of an external GET wear test device

Referring to FIG. 6, exemplary configurations of the electrical and control components of the wear sensor assembly 40 and a corresponding external GET wear test device 70 of the wear life sensing system are illustrated. The electrical and control components of the wear sensor assembly 40 may be enclosed within a wear sensor assembly housing 72. The illustrated embodiment of the wear sensor assembly 40 may include a sensor assembly controller 74 that may be capable of performing the processing necessary to determine whether the ground engaging tip 20 is worn to the point of requiring replacement. The sensor assembly controller 74 may include a processor 76 for executing a GET wear life testing routine performed by the wear sensor assembly 40. The processor 76 may be operatively connected to a memory 78 that may have a read only memory (ROM) 80 for storing programs, and a random access memory (RAM) 82 serving as a working memory area for use in executing a flight control program stored in the ROM 80. Although the processor 76 is shown, it is also possible and contemplated to use other electronic components such as a microcontroller, an application specific integrated circuit (ASIC) chip, or any other integrated circuit device.

The wear sensor assembly 40 also includes a distance sensor 84 operatively connected to the sensor assembly controller 74. The distance sensor 84 is capable of transmitting the output distance sensor signals 52 into the tip body 22, and receiving the reflected distance sensor signals 54 that bounce back from the exterior surface 24 and the wear sensing body 60. The distance sensor 84 can be any appropriate transceiver capable of transmitting and receiving sound waves through the tip body 22 such as, for example, an ultrasonic transceiver. The distance sensor 84 may include a transmitter 86 for transmitting the output distance sensor signals 52, and a receiver 88 for detecting the reflected distance sensor signals 54. The distance sensor 84 is also capable of receiving transmission command signals from the sensor assembly controller 74 that cause the distance sensor 84 to transmit the output distance sensor signals 52, and to transmit sensed distance signals to the sensor assembly controller 74 having values indicative of the reflected distance sensor signals 54.

A sensor assembly communications module 90 may be operatively connected to the sensor assembly controller 74. The sensor assembly communications module 90 is capable of being controlled by the sensor assembly controller 74 to perform wireless communications with the external GET wear test device 70 to receive wear test request messages from the external GET wear test device 70 and communicate GET replacement messages to the external GET wear test device 70. The wear sensor assembly housing 72 may also house a sensor assembly power source 92 providing power to the sensor assembly controller 74, the distance sensor 84 and the sensor assembly communications module 90. In one embodiment, the sensor assembly power source 92 is fully self-contained, and has sufficient storage capability to provide power for the wear sensor assembly 40 for the designed duration of the useful wear life of the ground engaging tip 20. In alternative embodiments, the sensor assembly power source 92 may be connected to an external power source (not shown) that may be part of the implement assemblies 1, 6 or the machine in which the ground engaging tips 20 are implemented. A power transfer connection may be provided via a power cable operatively connected between the sensor assembly power source 92 and the external power source and extending through the wear sensor cavity cap 48.

The external GET wear test device 70 is configured to communicate with the wear sensor assembly 40 and to control the wear testing of the ground engaging tip 20. The external GET wear test device 70 may be a standalone unit such as a handheld device that may be used by a machine operator or maintenance worker to initiate the GET wear life testing routine. Alternatively, the external GET wear test device 70 may be integrated into the machine that will be using the implement 2, 7 with the ground engaging tips 20. The components described herein may be added to the machine, or existing machine components may be modified to provide the functionality of the external GET wear test device 70, such as electronic control modules (ECMs), user interface devices and communications modules. Still further, the external GET wear test device 70 may be implemented at a remote location such as a back office or control center for the owner of the machine. These and additional alternatives are contemplated by the inventor as having use in GET wear life testing in accordance with the present disclosure.

Depending on the particular implementation, the external GET wear test device 70 may have a test device housing 100 enclosing the electrical and control components. The external GET wear test device 70 as illustrated includes a test device controller 102 capable of controlling the performance of the GET wear life testing routine, and communications with the wear sensor assemblies 40 of the ground engaging tips 20 and the operators and maintenance workers. Similar to the sensor assembly controller 74, the test device controller 102 may include a processor 104 and a memory 106 having a ROM 108 and a RAM 110. The external GET wear test device 70 further includes a test device communications module 112 that is capable of exchanging communication signals with the sensor assembly communications module 90. A test device power source 114 provides power to the other components of the external GET wear test device 70. In alternative embodiments, the external GET wear test device 70 may be connected to an external power source by appropriate wiring.

The external GET wear test device 70 also may include interface devices for communicating with the machine operator or maintenance worker requesting a wear life test. The external GET wear test device 70 may have one or more input devices 116 for inputting commands for the test device controller 102. Of particular relevance to the present disclosure are operator input devices 116 providing commands and data related to the operation of the wear sensor assembly 40 to execute a GET wear life testing routine on the ground engaging tip 20. The input devices 116 may be as simple as a "TEST" button that is pressed to cause the test device controller 102 to execute the GET wear life testing routine, or a graphical user interface such as a touchscreen that may allow a user to enter various types of information and test commands. The output devices 118 may be operatively connected to the test device controller 102 to receive output command signals from the test device controller 102. The output device(s) 118 may be any device capable of providing a sensory perceptible output to the operator, such as visual display devices, lamps, speakers, and the like. The information communicated to the operator may include an indication that a ground engaging tip 20 is fully or partially worn to the maximum GET wear point 62, identification information for one or more ground engaging tips 20 that are ready for replacement, and the like, during and after the performance of the wear life test routine.

Figure 7:
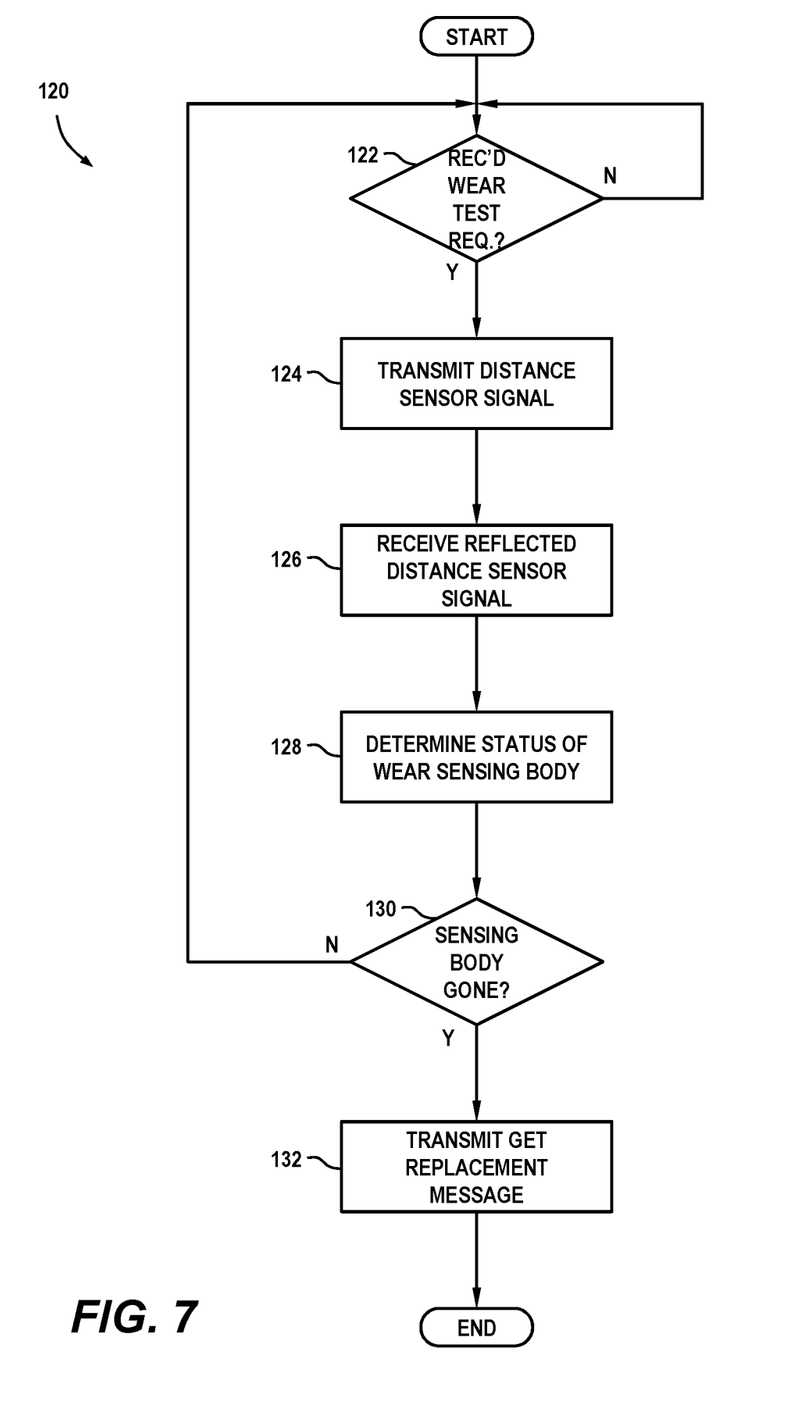
FIG. 7 is a block diagram of a GET wear life testing routine in accordance with the present disclosure that may be executed by the wear life sensing system of FIGS. 5 and 6.

FIG. 7 illustrates an exemplary GET wear life testing routine 120 that may be executed by the wear sensor assembly 40 and the external GET wear test device 70 of the wear life sensing system. The GET wear life testing routine 120 may be performed at each of the GETs, such as the ground engaging tips 20, on the implement 2, 7 simultaneously, or may be performed at different times, such as more frequently on the GETs that have been in place on the implement 2, 7 for the longest time and are therefore likely closest to the end of their wear life, and less frequently on new GETs that have been installed more recently in place of worn out GETs. The selective testing of the GETs may be accomplished by assigning a unique identifier to each GET that will be stored at the memory 78, or by other methods discussed further hereinafter.

The GET wear life testing routine 120 may begin at a block 122 where the sensor assembly controller 74 may determine whether a wear test request message has been received at the sensor assembly communications module 90. The wear test request message may be transmitted from the external GET wear test device 70 in response to an operator's inputting a GET wear test request command at one of the input devices 116. Alternatively, the test device controller 102 may be configured to determine when a wear life test should be performed based on factors such as the time since the last wear life test, the amount of time the GETs have been installed on the implement 2, 7, the amount of time the work machine has been actively performing material handling functions, and the like. When the test device controller 102 determines that the wear life test should be performed, the test device controller 102 may cause the test device communications module 112 to transmit the wear life test request message to the GET(s) to be tested. In further alternative embodiments, the sensor assembly controller 74 of each GET may be configured to perform a similar calculation for the appropriate time to perform a wear life test, and the logic performed at the block 122 may be an evaluation by the sensor assembly controller 74 of whether it is an appropriate time for the wear life test.

If a wear life test request message has not been received at the sensor assembly communications module 90, or the sensor assembly controller 74 otherwise determines that it is not time to perform the wear life test, control passes back to the block 122 to continue evaluating whether the wear life test should be performed. If a wear life test request message is received or it is time for a GET wear life test at the block 122. Control passes to a block 124 where the sensor assembly controller 74 causes the distance sensor 84 to output the output distance sensor signals 52. In the illustrated embodiment, the transmitter 86 of the ultrasonic transceiver 84 will output ultrasonic waves through the conductive gel 50 and into the tip body 22 in the general direction of the ground engaging and 28. As the ultrasonic waves travel through the tip body 22, they are fully or partially reflected when they reach the wear sensing body 60 or the exterior surface 24 and experience changes in the material density and the speed of sound.

The reflection of the output distance sensor signals 52 off the wear sensing body 60 creates reflected distance sensor signals 54 back in the direction of the wear sensor assembly 40. Depending on the shape of the exterior surface 24 at a given time, some reflected distance sensor signals 54 from the exterior surface 24 may also be directed back to the wear sensor assembly 40. To determine the presence of and distance to the wear sensing body 60, control of the GET wear life testing routine 120 passes to a block 126 where the reflected distance sensor signals 54 are received at the distance sensor 84. Upon receipt, the distance sensor 84 transmits corresponding messages to the sensor assembly controller 74.

Figure 8:
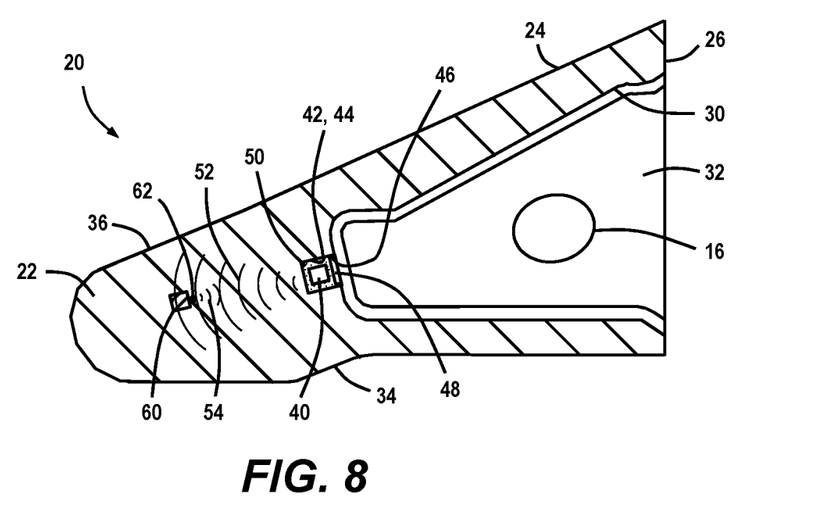
FIG. 8 is the cross-sectional view of the ground engaging tip of FIG. 5 worn down but not at the end of its useful wear life.

When the reflected distance sensor signals 54 are received at the distance sensor 84 and the messages are transmitted to the sensor assembly controller 74, control passes to a block 128 where the sensor assembly controller 74 determines a status of the wear sensing body 60. The sensor assembly controller 74 may be configured to use techniques known in the art for determining the distance to an object based on sound waves. Because the wear sensing body 60 is embedded in and stationary within the GET body, such as the tip body 22, the reflected distance sensor signals 54 from the wear sensing body 60 will be constant as long as the wear sensing body 60 is still in the GET body regardless of the shape of the exterior surface 24. Consequently, the reflected distance sensor signals 54 for the wear sensing body 60 will be consistent when the GET is new as shown for the ground engaging tip 20 in FIG. 5, or is partially worn down as shown in FIG. 8, but not worn down to the maximum GET wear point 62. As long as the reflected distance sensor signals 54 remain consistent, the sensor assembly controller 74 will determine that the wear sensing body 60 is present and the GET is not at the end of its useful wear life.

Figure 9:
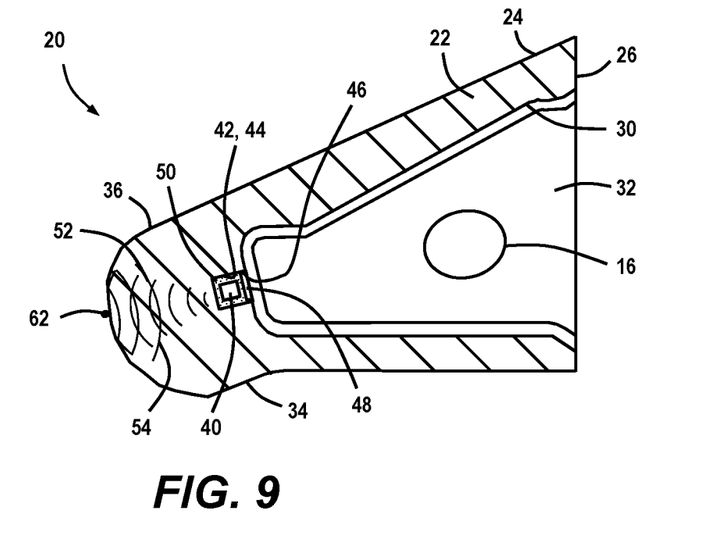
FIG. 9 is the cross-sectional view of the ground engaging tip of FIG. 5 worn down to a maximum GET wear point.

After the sensor assembly controller 74 determines the status of the wear sensing body 60 at the block 128, control passes to a block 130 where the sensor assembly controller 74 uses the status of the wear sensing body 60 to determine whether the GET should be replaced. If the sensor assembly controller 74 determines that the wear sensing body 60 is still present at the block 130, the GET does not need to be replaced and control passes back to the block 122 to wait for the next tip wear life test request. If the sensor assembly controller 74 determines that the wear sensing body 60 is gone, then the GET is at the end of the its useful wear life. FIG. 9 illustrates an example of the ground engaging tip 20 worn down to the point that the wear sensing body 60 is worn away from the tip body 22. As illustrated, the tip body 22 has also worn past the maximum GET wear point 62 since the previous wear life test. Without the wear sensing body 60, the output distance sensor signals 52 reflects off the exterior surface 24. The character of the reflected distance sensor signals 54 changes to indicate the decreased distance to the exterior surface 24. In response to this change in the character and distance, the sensor assembly controller 74 determines that the wear sensing body 60 is gone from the tip body 22 and, correspondingly, that the ground engaging tip 20 should be replaced.

When the sensor assembly controller 74 determines that the wear sensing body 60 is gone at the blocks 128, 130, control passes to a block 132 where the sensor assembly controller 74 causes the sensor assembly communications module 90 to transmit a GET replacement message to the external GET wear test device 70. The GET replacement message may include an indication of the specific GET that transmitted the GET replacement message. For example, each GET may be assigned a unique identifier that is stored in the memory 78 of the wear sensor assembly 40. The GET placement message may then be formatted with the unique identifier so that the operator of the external GET wear test device 70 knows which GET requires replacement. When the GET replacement message is received at the test device communications module 112, the test device controller 102 will cause the output device 118 to produce a sensory perceptible output to the operator, such as a flashing light, a notification sound, or a message on a visual display, alerting the operator that the GET should be replaced. After the GET replacement message is transmitted at the block 132, the GET wear life testing routine 120 may terminate.

Figure 10:
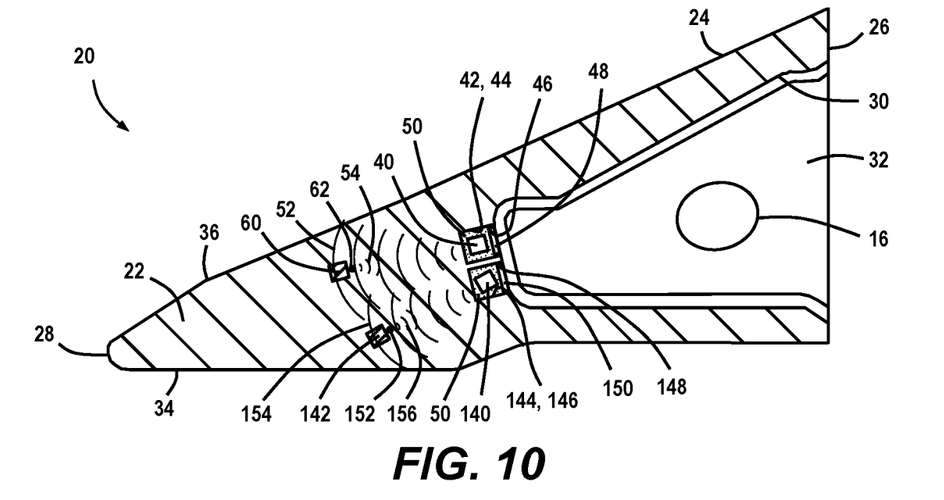
FIG. 10 is the cross-sectional view of the ground engaging tip of FIG. 5 with an alternative embodiment of the wear life sensing system having a second wear sensor assembly and a second wear sensing body proximate a second maximum GET wear point.

The GET may be modified as necessary to ensure that the wear status of the GET is known accurately and the GET can be replaced in a timely manner when it reaches the end of its useful wear life. Referring to FIG. 10, the GET in the form of the ground engaging tip 20 is configured to detect wear at multiple locations. This may be desirable if the ground engaging tip 20 or other GETs may have differing wear patterns depending on the use of the implement 2, 7. For example, the ground engaging tip 20 may wear from the ground engaging end 28 toward the adapter connection end 26 as shown in the sequence of FIGS. 5, 8, 9 if the implement 2, 7 digs into the work material, or the ground engaging tip 20 may wear up from the bottom surface 34 if the implement 2, 7 does a significant amount of scraping along the ground. To account for the latter wear pattern, the ground engaging tip 20 may include a second wear sensor assembly 140 and a second wear sensing body 142 within the tip body 22.

The second wear sensor assembly 140 may have a similar configuration as the first wear sensor assembly 40, with a second sensor assembly controller 74, a second processor 76, a second memory 78, a second distance sensor 84, and a second sensor assembly communications module 90. The wear sensor cavity 44 may be large enough to house both wear sensor assembly 40, 140, or a second wear sensor cavity surface 144 may define a second wear sensor cavity 146 with a second wear sensor cavity opening 148 closed by a second wear sensor cavity cap 150 to retain the second wear sensor assembly 140 and conductive gel 50 within the second wear sensor cavity 146. The second wear sensing body 142 is embedded in the GET body proximate a second maximum GET wear point 152 for wear up from the bottom surface 34. The second wear sensor assembly 140 may be directed at the second wear sensing body 142 so that second output distance sensor signals 154 reflected off the second wear sensing body 142 to generate second reflected distance sensor signals 156. The second wear sensor assembly 140 may execute the GET wear life testing routine 120 in the manner described above so that the GET replacement message is transmitted when either of the wear sensing bodies 60, 142 is worn away from the GET body. The wear sensor assemblies 40, 140 and the wear sensing bodies 60, 142 may be positioned at alternative locations that may indicate when it is desirable to replace the GET, and additional wear sensor assemblies 40, 140 and wear sensing bodies 60, 142 may be used within the GETs.

Figure 11:
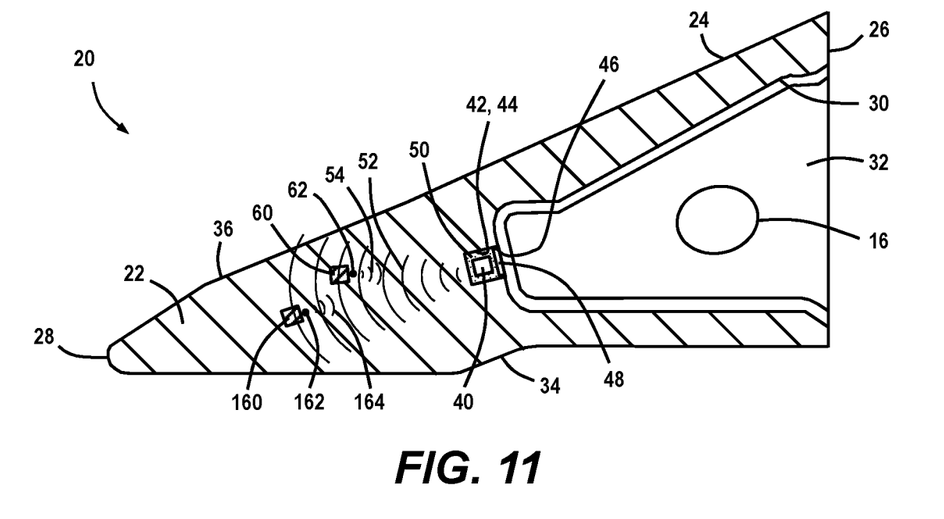
FIG. 11 is the cross-sectional view of the ground engaging tip of FIG. 5 with a further alternative embodiment of the wear life sensing system having a second wear sensing body proximate a partial GET wear point.

FIG. 11 illustrates a further alternative embodiment where the wear condition of the GET is determined and communicated to the operator at intermediate points as the GET body wears toward the maximum GET wear point 62. As shown, a second wear sensing body 160 is embedded in the tip body 22 at a partial GET wear point 162. The second wear sensing body 160 will create second reflected distance sensor signals 164 that are received at the distance sensor 84. With multiple wear sensing bodies 60, 160, the sensor assembly controller 74 may execute a modified GET wear life testing routine 170 shown in FIG. 12. The modified GET wear life testing routine 170 may start with blocks 122, 124, 126 as described above. Control may then pass to a block 172 where the sensor assembly controller 74 may determine the statuses of all the wear sensing bodies 60, 160 from the reflected distance sensor signals 54, 164. The reflected distance sensor signals 54, 164 will be consistent while the wear sensing bodies 60, 160 are still embedded in the GET body, and will change as the wear sensing bodies 60, 160 are worn away in turn. If no wear sensing bodies 60, 160 are gone at the block 130, control passes back to the block 122 until the next wear test request.

Figure 12:
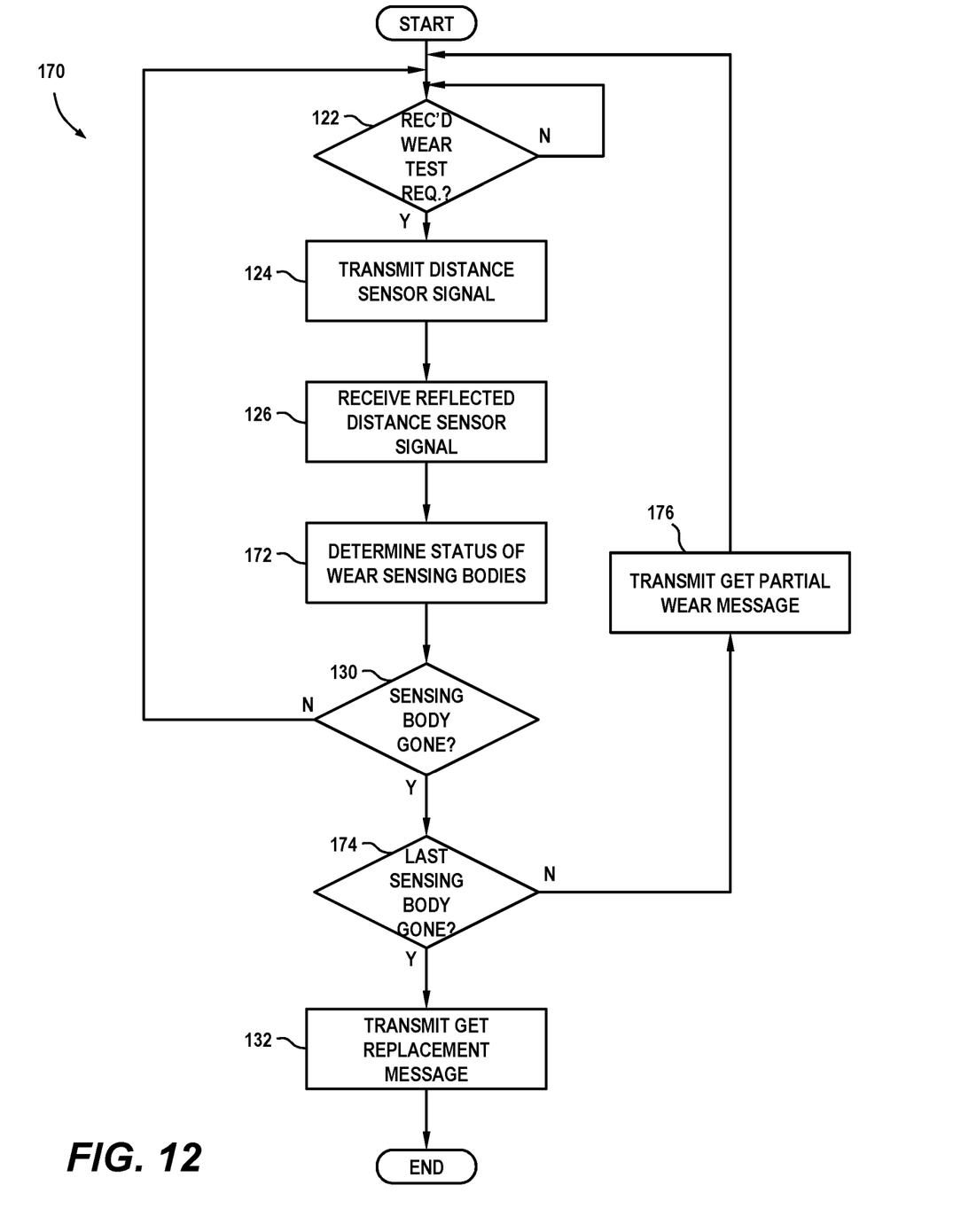
FIG. 12 is a block diagram of a modified GET wear life testing routine in accordance with the present disclosure that may be executed by the wear life sensing assembly of FIGS. 5 and 6 with the alternative embodiment of the wear life sensing system of FIG. 11.

If a wear sensing body 60, 160 is determined to be gone from the GET body at the block 130, control passes to a block 174 to determine whether the last wear sensing body 60 is gone. If the wear sensing body 60 is not gone, the GET is not yet at the end of its useful wear life, but the GET body has worn to the partial GET wear point 162. In this situation, control passes to a block 178 to transmit a GET partial wear message to the external GET wear test device 70. The external GET wear test device 70 may respond by outputting an appropriate message to the operator at the output device 118. The message may alert the operator or maintenance workers so that replacement of the GET may be scheduled before the GET body wears to the maximum GET wear point 62. If the sensor assembly controller 74 determines that the last wear sensing body 60 is gone at the block 174, control passes to the block 132 to transmit the GET replacement message as discussed above.

INDUSTRIAL APPLICABILITY

The wear life sensing system in accordance with the present disclosure may provide for accurate and timely determination that the GETs have reached the ends of their useful wear lives and should be replaced so that the work machines can operate most efficiently. The wear life sensing system and the GET wear life testing routines 120, 170 utilize known methods of non-destructive inspection using sound waves to detect and determine distances to objects or irregularities within solid bodies. The wear sensing bodies 60, 142, 160 embedded within the GETs provide fixed reference points for determining at a minimum when the GETs should be replaced, and can provide intermediate wear indications when the GETs are partially worn. As long as the wear sensing bodies 60, 142, 160 are present in the GETs, the GETs have remaining useful wear life and provide acceptable ground engaging performance for the implements 2, 7. When the wear sensing bodies 60, 142, 160 are no longer present in the GETs, the operator or maintenance works will be notified with reliable information that the GETs are at the ends of their useful wear lives.

While the preceding text sets forth a detailed description of numerous different embodiments, it should be understood that the legal scope of protection is defined by the words of the claims set forth at the end of this patent. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims defining the scope of protection.

It should also be understood that, unless a term was expressly defined herein, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to herein in a manner consistent with a single meaning, that is done for sake of clarity only so as to not confuse the reader, and it is not intended that such claim term be limited, by implication or otherwise, to that single meaning.

What is claimed is:

1. A ground engaging member of a ground engaging assembly for an implement of a work machine that engages a work material to dig into the work material, the ground engaging member comprising:
    a member body extending from a leading end to a trailing end,
        the member body having an internal surface defining a cavity therein, the cavity having a concavity that faces away from the leading end along a longitudinal direction, the longitudinal direction extending from the leading end to the trailing end,
        the member body being fabricated from a ground engaging tool (GET) body material having a GET body material density; and
    a first wear sensing body embedded in the member body between the cavity and the leading end along the longitudinal direction, the first wear sensing body being fabricated from a wear sensing body material having a wear sensing body material density that is not equal to the GET body material density.

2. The ground engaging member of claim 1, wherein the first wear sensing body is completely engulfed within the member body.

3. The ground engaging member of claim 1, wherein the member body has an external surface that defines a taper along the longitudinal direction, a thickness of the taper adjacent the leading end being less than a thickness of the taper adjacent the trailing end.

4. The ground engaging member of claim 1, wherein the GET body material density is greater than the wear sensing body material density.

5. The ground engaging member of claim 4, wherein the wear sensing body material is carbon.

6. The ground engaging member of claim 4, wherein the wear sensing body material is air disposed within a wear sensing cavity defined within the member body.

7. The ground engaging member of claim 1, further comprising a second wear sensing body embedded in the member body between the cavity and the first wear sensing body along the longitudinal direction, the second wear sensing body being fabricated from the wear sensing body material.

8. The ground engaging member of claim 7, wherein the second wear sensing body is located below the first wear sensing body along a transverse direction, the transverse direction being transverse to the longitudinal direction.

9. The ground engaging member of claim 1, wherein the trailing end is configured to fix the ground engaging member to the implement of the work machine, and the leading end is shaped to penetrate the work material into which the implement digs.

10. The ground engaging member of claim 1, further comprising a sensor disposed within the cavity, the sensor being configured to generate a signal that is indicative of a distance between the sensor and the first wear sensing body.

11. The ground engaging member of claim 1, wherein the ground engaging member at least partly composes one of a tooth assembly, a corner guard, an edge protector assembly, and a base edge of the implement.

12. A ground engaging assembly for an implement of a work machine that engages a work material to dig into the work material, the ground engaging assembly comprising:
    a plurality of member bodies, each member body of the plurality of member bodies extending from a leading end to a trailing end,
        each member body having an internal surface defining a cavity therein, the cavity having a concavity that faces away from the leading end along a longitudinal direction, the longitudinal direction extending from the leading end to the trailing end,
        each member body being fabricated from a ground engaging tool (GET) body material having a GET body material density; and
    a first wear sensing body embedded in each member body between the cavity and the leading end along the longitudinal direction, the first wear sensing body being fabricated from a wear sensing body material having a wear sensing body material density that is not equal to the GET body material density.

13. The ground engaging assembly of claim 12, wherein a first member body of the plurality of member bodies at least partly composes one of a tooth assembly, a corner guard, an edge protector assembly, and a base edge of the implement.

14. The ground engaging assembly of claim 12, wherein a first member body of the plurality of member bodies at least partly composes a tooth assembly of the implement, and
    a second member body of the plurality of member bodies at least partly composes one of a corner guard, an edge protector assembly, and a base edge of the implement.

15. The ground engaging assembly of claim 12, wherein the trailing end is configured to fix the ground engaging member to the implement of the work machine, and the leading end is shaped to penetrate the work material into which the implement digs.

16. The ground engaging assembly of claim 12, further comprising a plurality of sensors, each sensor of the plurality of sensors being disposed with the cavity of a corresponding member body of the plurality of member bodies, each sensor being configured to generate a signal that is indicative of a distance to the first wear sensing body of the corresponding member body.

17. The ground engaging assembly of claim 12, wherein the GET body material density is greater than the wear sensing body material density.

18. An implement of a work machine that engages a work material to dig into the work material, the implement comprising:
  a plurality of member bodies, each member body of the plurality of member bodies extending from a leading end to a trailing end,
    each member body having an internal surface defining a cavity therein, the cavity having a concavity that faces away from the leading end along a longitudinal direction, the longitudinal direction extending from the leading end to the trailing end,
    each member body being fabricated from a ground engaging tool (GET) body material having a GET body material density; and
  a first wear sensing body embedded in each member body between the cavity and the leading end along the longitudinal direction, the first wear sensing body being fabricated from a wear sensing body material having a wear sensing body material density that is not equal to the GET body material density.

19. The implement of claim 18, wherein the implement is one of an excavator bucket and a loader bucket.

20. The implement of claim 18, wherein a first member body of the plurality of member bodies at least partly composes one of a tooth assembly, a corner guard, an edge protector assembly, and a base edge of the implement.

* * * * *